(12) United States Patent
Hobbs et al.

(10) Patent No.: US 8,562,588 B2
(45) Date of Patent: *Oct. 22, 2013

(54) IRREVERSIBLE ELECTROPORATION AND TISSUE REGENERATION

(75) Inventors: Eamonn P. Hobbs, Queensbury, NY (US); James G. Lovewell, San Leandro, CA (US); Robert M. Pearson, San Jose, CA (US)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/556,510

(22) Filed: Jul. 24, 2012

(65) Prior Publication Data

US 2012/0289888 A1 Nov. 15, 2012

Related U.S. Application Data

(63) Continuation of application No. 12/703,355, filed on Feb. 10, 2010, now Pat. No. 8,231,603.

(60) Provisional application No. 61/151,305, filed on Feb. 10, 2009.

(51) Int. Cl.
*A61M 31/00* (2006.01)

(52) U.S. Cl.
USPC ............. 604/506; 604/507; 604/522; 606/41

(58) Field of Classification Search
USPC ............. 604/20–21, 501, 506–507, 511, 522; 606/32, 41
See application file for complete search history.

(56) References Cited

U.S. PATENT DOCUMENTS

| 7,565,208 | B2* | 7/2009 | Harris et al. | 607/116 |
| 8,109,926 | B2* | 2/2012 | Azure | 606/41 |
| 8,231,603 | B2* | 7/2012 | Hobbs et al. | 604/522 |
| 2009/0281477 | A1* | 11/2009 | Mikus et al. | 604/21 |

* cited by examiner

*Primary Examiner* — Theodore Stigell
(74) *Attorney, Agent, or Firm* — Ryan D. Artis

(57) ABSTRACT

A method and device are herein described to treat a target region of tissue, using at least one energy delivery device coupled to a power source and positioned in a treatment position so as to irreversibly electroporate tissue to ablate a target region, and introduce regenerative materials into a treated region.

26 Claims, 14 Drawing Sheets

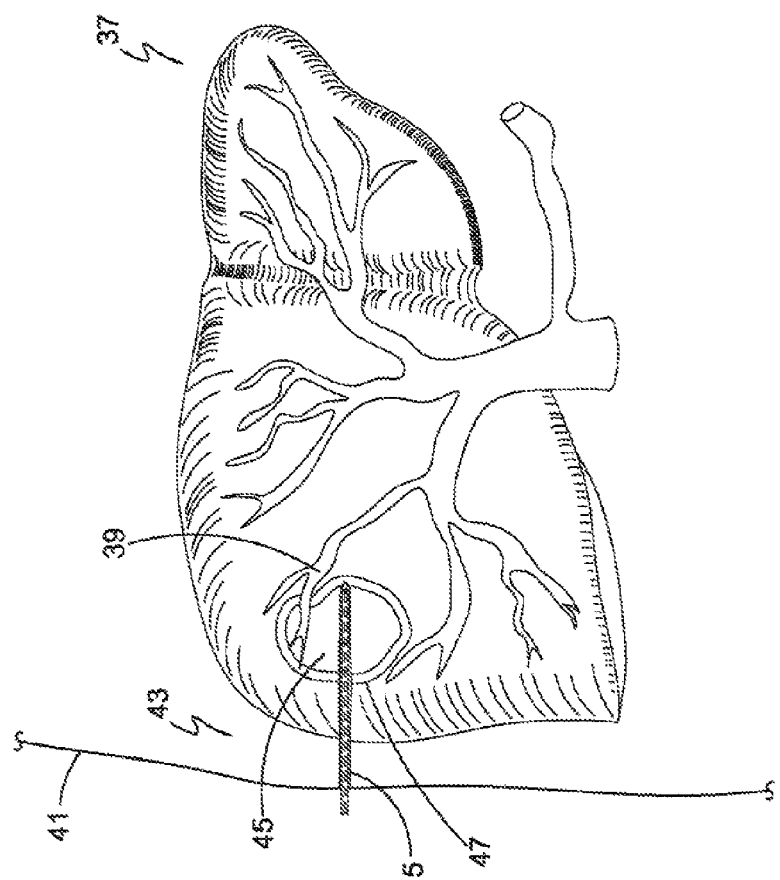

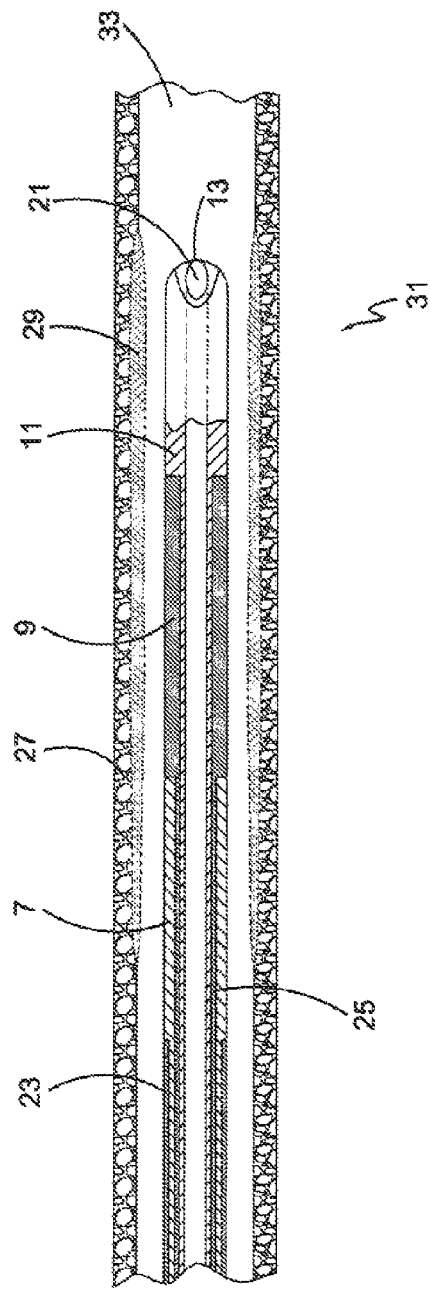
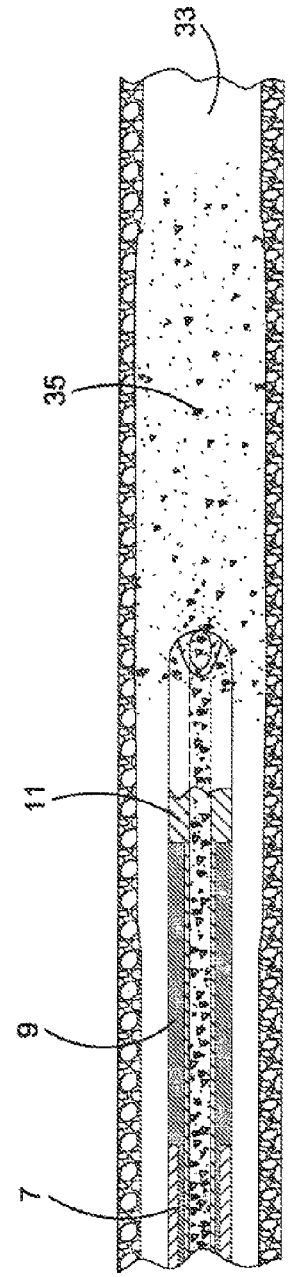
FIG. 7A
FIG. 7B

IRREVERSIBLE ELECTROPORATION AND TISSUE REGENERATION

CROSS REFERENCE TO RELATED APPLICATIONS

This application is a continuation of U.S. Pat. No. 8,231,603, filed Feb. 10, 2010, which claims priority to U.S. Provisional Application Ser. No. 61/151,305, Irreversible Electroporation and Tissue Regeneration, filed Feb. 10, 2009, which is incorporated herein by reference.

BACKGROUND OF THE INVENTION

1. Field of the Invention

The present invention relates generally to advancements in medical treatment. More specifically, this present invention is related to effectively treating a target region of tissue with Irreversible Electroporation (IRE), followed by introduction of regenerative materials leading to regrowth, restructuring, and cellular repopulation of the treated region.

2. Description of the Related Art

Tissue ablation is a medically necessary activity with destructive effects leading to cellular death within a target region (also herein called target tissue). Historically this endeavor has included a series of methods, each with varying degrees of effectiveness and subsequent levels of unintended consequences including adverse effects to surrounding tissue. Depending on the method used for tissue ablation and any underlying pathophysiology related to the medical treatment, the patient may have remaining tissue that is damaged, disorganized, and in need of repair. This is due to the fact that ablation techniques used historically have been nonselective in that they mediate cell death with methods such as extreme heat or cold. These methods will nonselectively and adversely affect blood vessels, nerves, and connective structures adjacent to the ablation zone. Disruption of the nerves locally impedes the body's natural ability to sense and regulate homeostatic and repair processes at and surrounding the ablation region. Disruption of the blood vessels prevents removal or debris and detritus. This also prevents or impedes repair systems, prevents homing of immune system components, and generally prevents normal blood flow that could carry factors such as hormones to the area. Without the advantage of a steady introduction of new materials to a damaged area, reconstruction of the blood vessels and internal linings become retarded as redeployment of cellular materials is inefficient or even impossible. Therefore historical ablation treatments do not leave tissue in an optimal state for self-repair in regenerating the region.

Recent developments offer an opportunity to advance the regenerative process following ablation treatments. A recent development in tissue ablation involves the use of irreversible electroporation (IRE). IRE offers the advantage of being a nonthermal ablation technique, which avoids some of the adverse consequences associated with temperature changes of ablative techniques such as radiofrequency (RF) ablation, microwave ablation, or even cryoablation. In addition, IRE has been shown to have sparing effects on structural components, leaving blood vessels and connective structures intact. This provides the advantage of providing a scaffold system which could then be utilized to increase the rate of reconstruction in the rebuilding process of recovery following ablation.

IRE has been applied to the treatment of tissue using ablation, and this technology has the distinct advantage of inducing cell necrosis without raising the temperature of the ablation zone. More specifically IRE is a technology where electrical pulses in the range of nanoseconds to milliseconds are applied to tissue to produce cellular necrosis and irreversible cell membrane permeabilization. More precisely, IRE treatment acts by creating defects in the cell membrane that are nanoscale in size and that lead to a disruption of homeostasis while sparing connective and scaffolding structure and tissue. These points have been addressed in the following publications, which are hereby incorporated by reference: Lavee J. A Novel Nonthermal Energy Source for Surgical Epicardial Atrial Ablation: Irreversible Electroporation. The Heart Surgery Forum. Vol. 10(2):96-101 (2007), and U.S. Patent Application Publication Number US 20060293731 A1, "Methods and systems for treating tumors using electroporation," application Ser. No. 11/165,961 filed on Jun. 24, 2005.

A distinct advantage of the IRE technology is the sparing of surrounding tissue, and in fact the structure of surrounding bile ducts, blood vessels, and connective tissue remains intact following application of IRE. This technology has been described in the following two patent application publications which are hereby incorporated by reference: Patent Application Publication Number WO2005/06284A2, "Tissue Ablation with Irreversible Electroporation," as well as U.S. Patent Application Publication Number US 2007/0043345A1, "Tissue Ablation with Irreversible Electroporation," application Ser. No. 10/571,162.

By utilizing IRE in combination with advanced regenerative technologies, there exists a vast potential for regrowth, regeneration, and cellular repopulation in a treated region that far surpasses current treatment modalities. The reason for this starts with the fact that the IRE treatment leaves structures such as blood vessels and nerves intact and ends with the fact that there are technologies that can take advantage of that fact for increased regeneration capabilities. Specifically, the remaining vessels and connective tissues are structures that provide a scaffold that can be built upon. These vessels can also act as a conduit for new materials, while remaining nerves can act to assist monitoring and mediating of the local conditions. Meanwhile, the introduction of regenerative materials to these locations can take advantage of the remaining foundation to advance regeneration. One example of a component of regenerative materials that would work synergistically with the IRE technology would be stem cells.

Effective development and use of stem cells is also a relatively recent development and is an emerging branch of technology that offers vast potential for enhancing regenerative capacity for an organ or tissue. A stem cell can be defined as a cell capable of producing unaltered daughter cells continuously, and a cell that is also capable of producing daughter cells that have differentiated characteristics. In other words, stem cells producing progeny that are to have separate or distinguished fates will have undergone asymmetric division while those daughter cells having the same fate have undergone symmetric division.

These concepts have been described in the following two papers, hereby incorporated by reference:

Smith A., A Glossary for Stem Cell Biology. Nature Vol. 441(7097):1060-61 (2006).

Morrison S. J., Kimble J., Asymmetric and Symmetric Stem Cell Divisions in Development and Cancer, 441(7097) Nature 1068, 1068-74 (2006).

One advantage of utilizing stem cells in a regenerative process involves the ability of a small number of cells to repopulate an area since the dividing cells have less potential for exhaustion on division. In fact, there are a variety of stem cell categories, which can be grossly broken into totipotent, pluripotent, multipotent, and unipotent, which are indicated here with respective decreasing plasticity or potency. A second advantage of utilizing stem cells is that the cells can differentiate into one or more cell types depending on the milieu of factors in the host niche environment. The power of this capacity can potentially be utilized as an astounding regenerative tool of medicine that could combat tissue injury, lead to treatments for degenerative diseases, and the normal decline of aging. This concept has been addressed in the following two papers, hereby incorporated by reference:

Rando T. A. Stem Cells, Aging and the Quest for Immortality. Nature. Vol. 441(7097):1080-1086 (2006).

Ioannidou E., Therapeutic modulation of growth factors and cytokines in regenerative medicine, 12(19) Current Pharmaceutical Design. Vol. 12(19):2397 (2006).

Stem cells could also be used for therapies for progressive blindness, neurological disorders including stroke, Parkinson's disease, and multiple sclerosis, and also holds potential for treatment of heart disease. This concept has been discussed in the following three papers, hereby incorporated by reference:

Lindvall O., Kokaia Z., Stem cells for the treatment of neurological disorders. Nature. Vol. 441(7097): 1094-1096 (2006).

Couzin J., A Shot of Bone Marrow Can Help the Heart. Science. Vol 313: 1715-1716 (2006).

Srivastava D., Ivey K. N., Potential of Stem-Cell-Based Therapies for Heart Disease. Nature. Vol. 441(7097): 1097-1099 (2006).

This invention allows for the combined use of nonthermal ablation of undesired tissue through IRE with the introduction of regenerative materials that will allow the regrowth of tissue following ablation. A need exists for an apparatus and method for accomplishing effective ablation followed by introduction of regenerative materials so as to increase the rate of regrowth, the rate of reconstruction, and cellular repopulation of a region following ablation. There is a need for a method and device that can ultimately decrease patient recovery times in a significant number of different treatment situations through more effective regeneration. The proposed method and apparatus matches these needs and allows for an increased opportunity for regrowth in tissues through the introduction of regenerative materials that may include stem cells. The proposed method and apparatus also provides for a treatment that can be used widely; in tissues that naturally regenerate (to enhance the effectiveness and rate of regeneration), in tissues without significant natural regenerative powers, and in those with pathophysiological factors that may otherwise impede regenerations.

Applicant(s) believe(s) that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), applicant(s) will amend the specification to expressly recite the essential material that is incorporated by reference as allowed by the applicable rules.

BRIEF SUMMARY OF THE INVENTION

The present invention provides among other things a method and apparatus to advance medical treatment outcomes through the utilization of regenerative therapies following targeted nonthermal tissue ablation to return tissue of a treated region more rapidly and effectively to a non-pathological, normal, homeostatic state.

There exists a need in the art for a method and apparatus capable of providing a framework for tissue regeneration following the use of nonthermal tissue ablation such as IRE which effectively spares structural components leaving a structure upon which regeneration can be initiated. Nonthermal IRE ablation involves ablation where the primary method of cellular disruption leading to death is mediated via electroporation (rather than factors such as effects of or responses to heating). In certain embodiments, depending on the parameters mentioned (including time that the resulting temperature occurs), cellular death can be mediated via nonthermal IRE up to approximately 50.degree. C. A parameter can also be a voltage, amperage, pulse number, timing of pulses, or duration between pulses, or a combination of at least one of voltage, amperage, pulse number, timing of pulses, or duration between pulses.

There exists a need in the art for an invention that can provide ablative and regenerative therapies in a single method or apparatus, or in a simplified series of effective applications of regenerative materials so as to increase the effectiveness of treatments, provide components for cellular rebuilding and introduce factors inducing proliferative response and regrowth to advance objectives for patient recovery. The current invention includes a method and device for treating tissue wherein the device has a channel for release of materials or factors in a device also capable of electroporation.

The above and other purposes may be achieved using a method to nonthermally ablate tissue using irreversible electroporation and to introduce regenerative materials into the ablated area. This method provides, among other things, a patient with a potentially decreased recovery time through increased efficiency of tissue regrowth and reformation. Regenerative materials can be released through the same probe (or same device) that is used in ablation, thus leading to ablation directly followed by introduction of regenerative materials. Regenerative materials can also be released using a separate device such as syringe or second probe.

The above and other purposes may be achieved using regenerative materials of various qualities: those that are totipotent, pluripotent, multipotent, as well as unipotent (cells), as well as those that are autogeneic, isogeneic, allogeneic, and xenogeneic. Regenerative materials can also include a variety of cells obtained through a variety of mechanism, including: embryonic stem cells, adult stem cells, vascular endothelial cell precursors, mesodermal stromal cells; these cells may be obtained from the use of magnetic beads, optical sensors, electric fields, as well as dielectrophoresis. Cells within the regenerative materials also may have a variety of distinct markers, protein expressions, or genetic compositions. This variety allows for multiple purposes to be effectively met.

There exists a need in the art for an invention that can provide ablative and regenerative therapies in a single method or apparatus and that can be used in a wide variety of procedures. This purpose may be achieved using irreversible electroporation, a nonthermal ablation method and by introducing regenerative materials; which can be applied in percutaneous, laparoscopic, and open surgery procedures. The method can be used when the target tissue either actually is one of the following tissues or is within the following tissues: digestive, skeletal, muscular, nervous, endocrine, circulatory, reproductive, integumentary, lymphatic, urinary, and soft tissue. The method can be used to target tissue of or within a vessel, a liver, or lung tissue. The method can also be used singly or in combination in tissues that are in the pancreas, prostate, uterus, and brain. The method can also be used to target singly or in combination tissues that are benign, malignant, cancerous, neoplastic, preneoplastic, or tumorous.

The above and other purposes may be achieved by applying materials subsequent to ablation that will enhance the regenerative properties of remaining tissue. Once power has been used to lead to the effect of irreversible electroporation in a target region, the remaining tissue, that is still a target region (just in a different state of physiology or viability) may also be called a treated region. This treated region can then be altered so as to bring about regeneration of that remaining tissue. This can involve direct application of regenerative materials, or can first involve a release of factors to rebalance any altered conditions as a result of the ablation. These materials and factors may include singly and in combination VEGF, cytokines, and anti-inflammatory agents, water, ions, hormones, paracrine agents, pharmacological mediators and vasoreactive elements. To ensure complete regeneration, the materials may need to be applied acutely or chronically, from one time to many times. In various embodiments, regenerative materials such as stem cells are released at any given time in the ablation therapy, from multiple sources singly or in combination and simultaneously or nonsimultaneously.

The above and other purposes may be achieved by applying regenerative materials that can be used to reestablish normal linings and membranes and cellular networks. This can involve direct application of a variety of regenerative materials released singly or in combination, in whole, in part, or precursors of DNA, RNA, proteins, carbohydrates, sugars, lipids, enzymes, proteases, steroids, amino acids, purine bases, pyrimidine bases, deoxyribose sugar, ribose sugar, nucleosides, adenosine-triphosphate, and adenosine biphosphate, polysaccharides, proteoglycans, hyaluronic acid, collagen, fibronectin, elastin, laminin, and integrins. The regenerative material could also include singly or in combination smooth muscle cells, epithelial cells, endothelial cells, liver cells, lung cells, pancreatic cells, and bone cells. In embodiments where the regenerative materials that are applied include cells, at least one cell can be the same cell type as the primary cell type of the target region. The primary cell type would refer either to the most predominant cell in number or area or the cell type providing that area with its anatomical name (such as a liver cell in a liver).

The above and other purposes may be achieved through the use of a device that applies nonthermal irreversible electroporation and that is capable or releasing regenerative materials to the ablation site.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

In FIG. 1B the shaft is shown as one example of a shaft, particularly a needle.

FIG. 2A depicts a cross-sectional view of a liver with a target region of tissue within the liver, where a needle of a bipolar probe coupled to an IRE power source has been inserted into the target region of tissue within the liver and where the safety zone of ablation surrounding the target region in the liver as well as interstitial space and a skin surface are shown for perspective.

FIG. 7A illustrates a cross-sectional view of a blood vessel immediately after ablation of a blockage by IRE treatment using a bipolar probe shown within the vessel.

FIG. 7B illustrates a cross-sectional view of a blood vessel, at a later time point from FIG. 7A, after ablation of a blockage by IRE treatment using a bipolar probe shown within the vessel, where regenerative materials are being released from a channel in the bipolar probe.

Figure 1A:
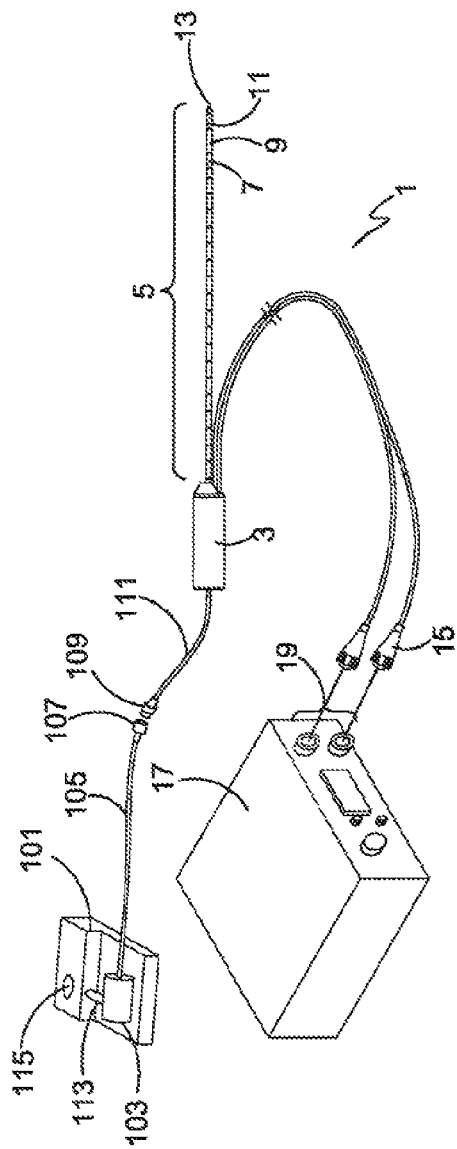
FIG. 1A depicts a perspective view of an IRE power source coupled to an energy delivery device that in this depiction is a bipolar probe utilized in the current invention. Also shown is a container for regenerative materials and an infusion pump for movement of materials.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention. It should be noted that there are many different and alternative configurations, devices and technologies to which the disclosed inventions may be applied. The full scope of the inventions is not limited to the examples that are described below. FIGS. 1-9 demonstrate utilization of the ablation and regenerative method and apparatus in a vessel and a target tissue within a liver and within a lung, and those these are simply representative. Target regions can include or be within digestive, skeletal, muscular, nervous, endocrine, circulatory, reproductive, integumentary, lymphatic, urinary, and soft tissue. The targets may also include benign or malignant, cancerous, neoplastic, preneoplastic, or tumors as stand-alone targets or targets found within another tissue (such as an organ or organ system). Ablation can be performed in each of laparoscopic, percutaneous, and open surgical procedures.

Regeneration refers to at least a partial restoration of an organ or tissue or new growth by an organism of organs and tissues that have been lost, removed, or injured. Regeneration can occur through several mechanisms, including but not limited to regrowth, restructuring, and cellular repopulation. Regrowth refers to growing, developing, and gradually increasing in size, number, value, or strength. Restructuring refers to a change in cell type, organ or tissue shape, pattern, or cell type or connectivity or arrangement than was originally present. Cellular repopulation refers to development of an area starting from a group of cells that can be exogenous from another part of the body or introduced in medical or experimental procedures to cause a specific effect of growth in a damaged area. Any of the processes or regeneration can be brought about or enhances via introduction of synthetics, exogenous materials mimicking internal, natural, agents and can be brought about by pharmacological reagents including agonists or antagonists to enhance regeneration.

Treatment position refers to a position such as, but not limited to, a position from the skin surface of a patient to the most distal edge of a target region where the energy delivery device is capable of treatment of a tissue to cause irreversible electroporation. Various treatment positions include placement such that irreversible electroporation occurs in a target region with at least a portion of the energy delivery device placed within the target region; also, an additional position includes wherein at least a portion of the energy delivery touches the surface of the target region. Yet other treatment positions include wherein at least a portion of the energy delivery device is adjacent, or near to the target region.

In one application of the invention, referring now to FIG. 1A, one embodiment of an energy delivery device 1 is depicted in FIG. 1A as a bipolar probe, including the handle 3 of the bipolar probe, shaft 5 (shown here as a needle 5), a proximal electrode 7, a distal electrode 11, an electrode spacer 9, a tip 13 of the bipolar probe shown here in this embodiment as a as three faced trocar tip, and a probe connector 15 of the bipolar probe. Hereafter the term energy delivery device and probe will be used interchangeably, with specific information regarding the type of probe being added to clarify monopolar, bipolar, and array types of energy delivery devices. The probe is coupled to a nonthermal power source 17, which has a positive and negative connector 19 for the bipolar probe 1. It is understood that in various embodiments the energy deliver device may be in the form of probes that are multiple monopolar, bipolar, or array formations; in embodiments using a bipolar as well as the array approach, there can be more than 1 anode or cathode on a given needle 5 of a probe. The monopolar embodiment can be used with two monopolar probes, one monopolar probe and a pad as known in the art, or in combination with bipolar probes or arrays of probes. Each of monopolar, bipolar, and array devices can be utilized together. In additional embodiments various portions of the probe are flexible or semi-flexible or articulating. In various embodiments the needle is of various flexibilities and may be articulating. In various embodiments the IRE power source can be a generator or other energy source and can be connected to a catheter that allows flexible entry into a lumen. This allows for utilization of the optimal probe for a given medical procedure.

Still referring to FIG. 1A, FIG. 1A also shows the following: a container 101 having a sealable cap 115 for introducing and removing material, an infusion pump 103, a first material transfer tube 113 between a container 101 and an infusion pump 103, and a second material transfer tube 105 and a third material transfer tube 111 that allow transfer of materials between the infusion pump 103 and the handle 3 of the bipolar probe. The second material transfer tube 105 has an end with a first fitting 107 that allows coupling to a second fitting 109 on one end of the third material transfer tube 111.

The container 101 represents any source of materials for introduction through the energy delivery device. The container can store one or more regenerative materials transiently, long-term, or permanently. The container can be programmable such that it stores materials at various temperatures, and can have or be coupled to a temperature controller to maintain regenerative materials at a selected temperature. The container can also have an internal portion that rotates or otherwise changes position so as to ensure materials stay in solution or do not adhere to the bottom or sides surface through gravity and other adhering forces. The container can have multiple regions each containing one or more regenerative materials that can be released singly or in combination to the target region of tissue through the needle 5 of the probe through one or more lumens and one or more couplings. The container can also be programmable regarding pressure or pH levels, and can have internal sensors so as to allow regulation of water volume or viscosity. The container is capable of containing any regenerative materials mentioned in this specification.

The sealable cap 115 allows for placing material within the container 101 and for removing material from container 101. The cap can comprise; one or more electrical or mechanical pieces that acts as a door to provide for moving of the materials; this can include a door, sealable shaft, rubber or plastic pieces allowing a syringe or container or hand to be placed within the interior of the container to replace or remove materials.

The infusion pump 103 provides for movement of the materials to the energy delivery device. The infusion pump 103 is capable of moving materials including but not limited to liquids, gases, semi-solids, and combinations of materials of various states from gas to liquid to solid. The infusion pump 103 is capable of moving any regenerative materials mentioned in this specification. In one various embodiments the infusion pump 103 moves stem cells. The infusion pump 103 can be programmable directly or remotely through any wireless system known in the art, and can deliver materials at any rate, including from introduction through drips to high pressure release of fluid. The programmable part can provide for regulation of volume or pressure of release. The infusion pump 103 can be powered via battery, or plug in to any wall outlet known in the art, from a generator, or can be powered from a diversion of power to the handle 3 of the probe. The infusion pump 103 can be programmed so as to release multiple regenerative materials. The infusion pump 103 can also be programmed to release one or more regenerative materials at various timepoints or the same or varying volumes.

In various embodiments the infusion pump 103 is capable of being a source for or storing regenerative materials (or both storing and being a source of) and in certain embodiments the infusion pump and container store materials. In various embodiments the infusion pump and container are contained in a unit that is part of the handle 3.

The first material transfer tube 113 allows movement of material between the container 101 and the infusion pump 103. In various embodiments the infusion pump 103 is located on the handle 3 of the probe. In other embodiments the container 101 and the infusion pump 103 are one unit and there is no material transfer tube 113.

The first fitting 107 allows coupling to the second fitting 109 and sealably couples one end of the second material transfer tube 105 to the second fitting 109 located on one end of the third material transfer tube 111 and provides for material movement through the handle 3 toward tissue through the needle 5 of the probe.

The second fitting 109 can couple with the first fitting 107. Second fitting 109 can also couple directly to a syringe or multiple syringes. In various embodiments the container is a syringe or a series of syringes; in various embodiments the second fitting 109 couples directly to the container 101 and in other embodiments there is no infusion pump. In certain embodiments manual power of the syringe plunger provides for movement of materials through the energy delivery device. In various embodiments the syringe is coated with a material on the interior to enhance survival or activity of regenerative material; the syringe can also be shaped or have a diameter such as to limit cellular shear stress.

The material transfer tubes (113, 105, 111) can each be made of any material allowing for transfer of materials. In various embodiments the tubes have coatings that prevent sticking of materials to the walls. In other embodiments the diameter is large enough to minimize shear stress on inserted cells.

Figure 1B:
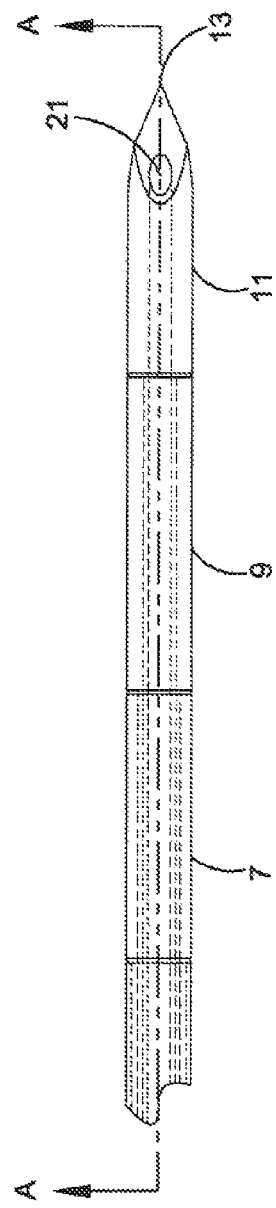
FIG. 1B depicts an enlarged side-view of the distal portion of the shaft of the bipolar probe.

FIG. 1B depicts an enlarged side-view of the distal portion of the needle of the bipolar probe. Shown are the proximal 7 and distal 11 electrodes separated by the electrode spacer 9, as well as a tip 13 of the bipolar probe shown here in this embodiment as a as three faced trocar tip. In addition, a channel 21 is illustrated which in one embodiment is hollow and allows for the movement of materials including liquids. The needle is any shaft capable of delivery of materials through the probe that is also capable of delivery of voltage. In certain embodiments the needle is capable of or adapted for movement of regenerative material.

Though FIG. 1B depicts an example embodiment with a channel shown as a single opening at the end of the probe, this is only one embodiment of many possible. The single channel could be centered within the needle of the probe, or could be placed nearer to one edge, and the end of the opening could be completely open or could be partially or fully covered with a solid, permeable, or semi-permeable covering, with or without micropores that allow for efficient release of regenerative materials for a given tissue. In additional embodiments there are a series of channels allowing for simultaneous or non-simultaneous, single or multiple releases of regenerative materials.

In certain embodiments the needle has a series of apertures at various points along its length so as to allow release of fluids and small particles. The release in all stated examples herein can be either active or passive release of regenerative materials. In addition, the IRE power source can be coupled to a catheter that can be used for ablation as well as for release of regenerative materials, and in various embodiments the catheter has a series of apertures along its length to release regenerative materials actively or passively.

Though FIGS. 1A and 1B show a channel for release of regenerative material from the needle of the probe, this is but one example of one configuration. The probe can be designed so as to be loaded with regenerative materials through one or more openings in the handle or the needle. In one embodiment the opening allows for the loading and releasing of regenerative materials in a straight line from the point of loading to the release point, so as to minimize turbulence and shear stress on any released cells or other materials. In another embodiment, there is a loading where there is an angle of greater than zero degrees from the point of loading to the point of release, such as an embodiment where there is an opening designed to receive materials from a syringe that can be coupled to the handle in a Y-shape.

Though FIG. 1B shows a single channel in a needle of a probe as a release point for regenerative material, the ablation and release of regenerative materials can be performed using an ablation probe singly or in combination with single or multiple catheters, syringes, or additional probes in cases including percutaneous, laparoscopic, and open surgery.

Figure 1C:
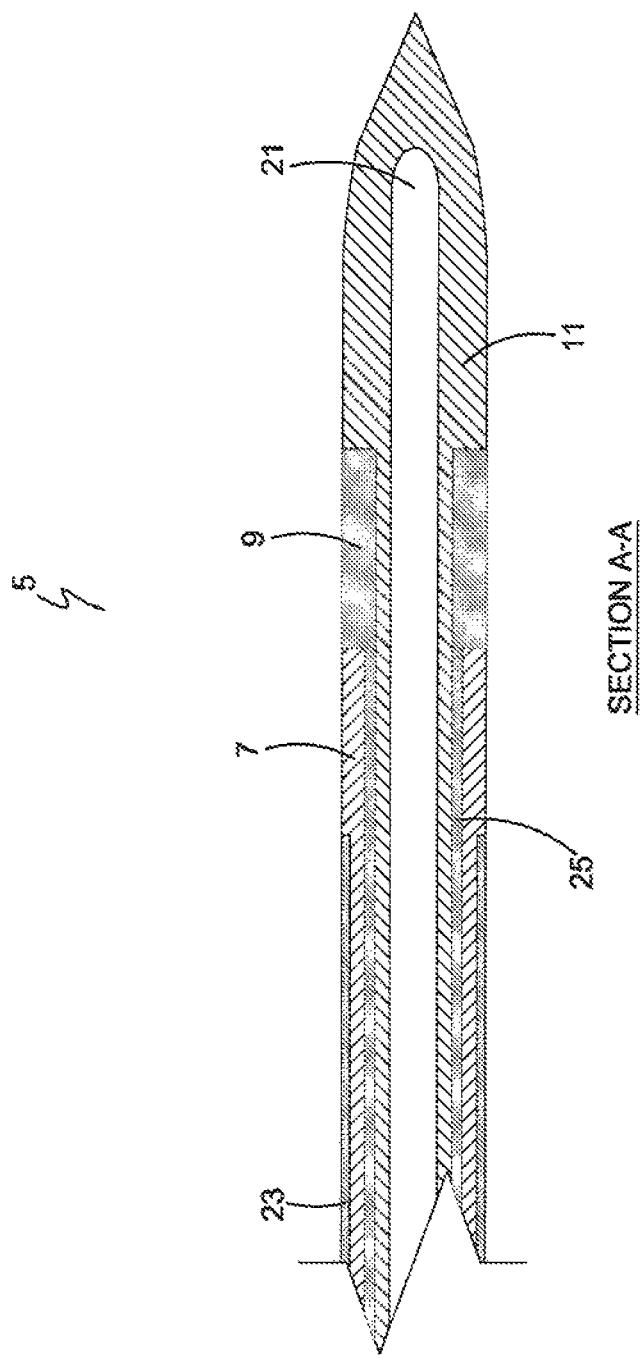
FIG. 1C depicts an enlarged cross-sectional view of a portion of the needle of the bipolar probe utilized in the current invention.

FIG. 1C is an enlarged cross-section of the distal portion of the needle of the bipolar probe from Section A-A of FIG. 1B. Depicted are the proximal 7 and distal 11 electrodes which are separated by a portion of insulative material reaching the outer surface of the needle and which is the electrode spacer 9. Also shown is the channel 21 within the probe, as well as the outer insulation 23 and inner insulation 25. In certain embodiments one or both of the outer and inner insulative materials is composed at least in part of polyester shrink material in single or multiple layers. The channel allows for the passage of materials such as fluids.

The channel can be used to release regenerative materials following ablation. In certain embodiments the channel can also be used to release factors to optimize the environment prior to the introduction of the regenerative materials. Optimizing refers to affecting the treated region in a way that either returns the region to a homeostatic condition or otherwise improves the likelihood, rate, or efficiency of regenerative materials in causing of effecting regeneration. This could involve active or passive rebalancing of tissue levels of materials following ablation, involving singly or in combination adding or altering the levels of water, ions, or factors such as hormones, paracrine agents and paracrine-type agents, and pharmacological mediators including vasoreactive elements. The introduced factors can be natural or synthetic and in certain cases can involve the introduction of a layer of cells. Optimization can be brought about through the introduction of factors.

In certain embodiments, either before or after the release of the regenerative materials (which may be released as a solution) or in combination or as part of the release of the regenerative solution, factors may be released singly or in combination including growth factors (to, in some cases, increase the growth of cells or in some cases to increase the growth rate of certain cells or all cells and in other cases to prevent the growth of certain cell types that may inhibit regeneration or lead to aberrant or undesirable regeneration) such as VEGF, cytokines, and anti-inflammatory agents. In certain embodiments these factors may increase the chance of successful regeneration. In certain embodiments, ion levels are altered singly or in combination, such as sodium, potassium, magnesium and calcium levels. In other embodiments the factors or ions are released with one or multiple cell types before, after, or in a simultaneous release with the cells to advance regeneration. In certain embodiments the regenerative material includes cells and factors that aim to restore tissue, membranes, or matrices. This can involve direct application of a variety of regenerative materials released singly or in combination, in whole, in part, or precursors of DNA, RNA, proteins, carbohydrates, sugars, lipids, enzymes, proteases, steroids, amino acids, purine bases, pyrimidine bases, deoxyribose sugar, ribose sugar, nucleosides, adenosinetriphosphate, and adenosine biphosphate, polysaccharides, proteoglycans, hyaluronic acid, collagen, fibronectin, elastin, laminin, and integrins. The regenerative material could also include singly or in combination smooth muscle cells, epithelial cells, endothelial cells, liver cells, lung cells, pancreatic cells, and bone cells.

FIG. 2A illustrates the ablation and regeneration concerning a target region in a liver. Specifically, this depicts a cross-sectional view, of a liver 37 with a target region of tissue 45 within the liver, where a needle 5 of a bipolar probe coupled to an IRE power source has been inserted into the target region 45 of tissue within the liver. There is a safety zone of ablation 47 surrounding the target region in the liver, though it is a very small layer and is shown here not necessarily to scale for ease of visualization. In addition, interstitial space 43 and a skin surface 41 outside the liver are shown for perspective.

Figure 2B:
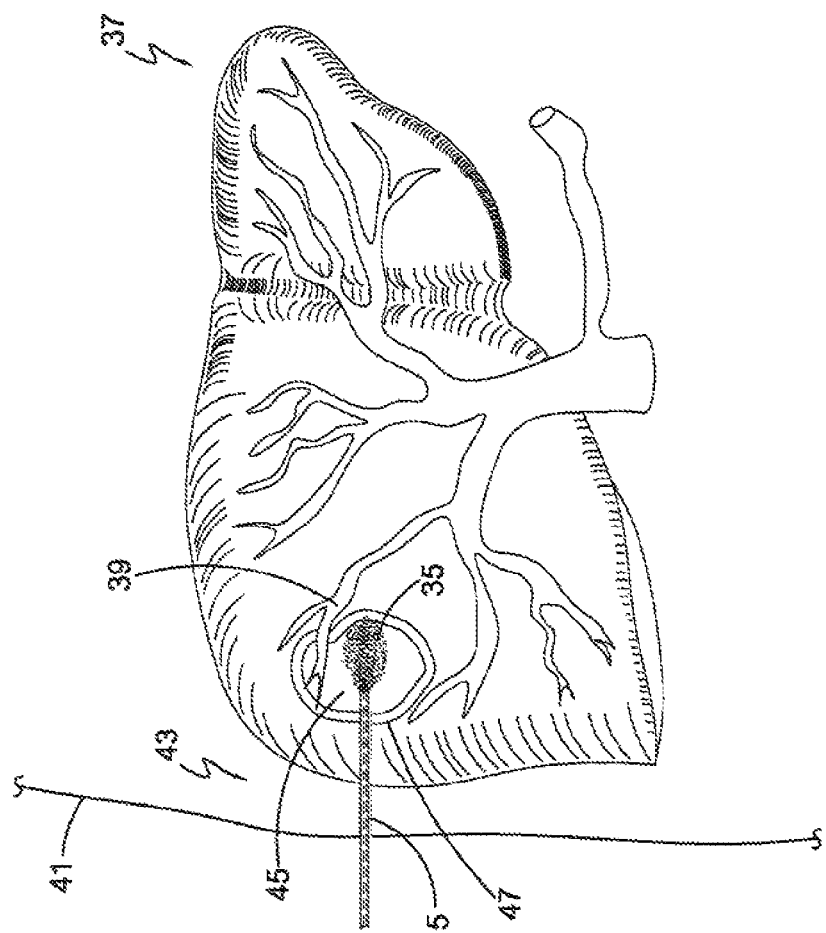
FIG. 2B is a cross-sectional view of the liver from FIG. 2A at a later time point, where IRE ablation has been performed, and regenerative materials are being released into the region that has been ablated with IRE energy within the liver through a channel in the needle of the bipolar probe.

FIG. 2B depicts the liver from FIG. 2A at a later time point once ablation has been performed. Structures shown include a liver 37, blood vessels 39 within the liver, a target region of tissue 45 within a liver, and a safety zone of ablation 47 surrounding the target region. Also shown is a needle of a bipolar probe 5, and regenerative materials 35 released from the probe into the previously ablated region.

The use of regenerative materials released in FIG. 2B depict regeneration in relation to a liver, though this is only one example among various applications of this technology. In various embodiments, release of regenerative materials involves ablation of target regions that can include or be within digestive, skeletal, muscular, nervous, endocrine, circulatory, reproductive, integumentary, lymphatic, urinary, and soft tissue. The targets may also include benign or malignant cancerous, neoplastic, preneoplastic, or tumors as stand-alone targets or targets found within another tissue (such as an organ or organ system).

In various embodiments released regenerative materials include stem cells that range from totipotent, to pluripotent, to multipotent, and to unipotent. In certain embodiments the stem cells utilized include cell lines currently available commercially. These stem cell lines may be human or other animal cell lines, which may or may not be genetically altered, or may be chimeras or may be released with factors enhancing regeneration obtained or derived from humans or nonhuman animals or both. For example, in certain embodiments released regenerative materials include a cell line available from ATCC (Manassas, Va.). An example embodiment would utilize a cell line with ATCC number SCRC-2002 with designation hESC BG01V of the cell type Embryonic Stem Cell. Other embodiments would include cell lines from any of the following: BresaGen, Inc. (Cell lines with provider codes such as Hesbgn-01, Hesbgn-02, Hesbgn-03, Hesbgn-04), Cellartis AB (Cell lines with provider codes such as Sahlgrenska 1, Sahlgrenska 2), ES Cell International (Cell lines with provider codes such as HES-1, HES-2, HES-3, HES-4, HES-5, HES-6), Technion-Israel Institute of Technology (Cell lines with provider codes such as I 3, I 3.2, I 3.3, I 4, I 6, I 6.2, J 3, J 3.2), University of California at San Francisco (Cell lines with provider codes such as HSF-1, HSF-6), as well as the Wisconsin Alumni Research Foundation (Cell lines with provider codes such as H1, H7, H9, H13, H14). Additional embodiments utilize cell lines from the National Stem Cell Bank. Yet an additional embodiment utilizes cells with at least one of the genetic code for or expressed marker of SSEA-1.

Figure 3A:
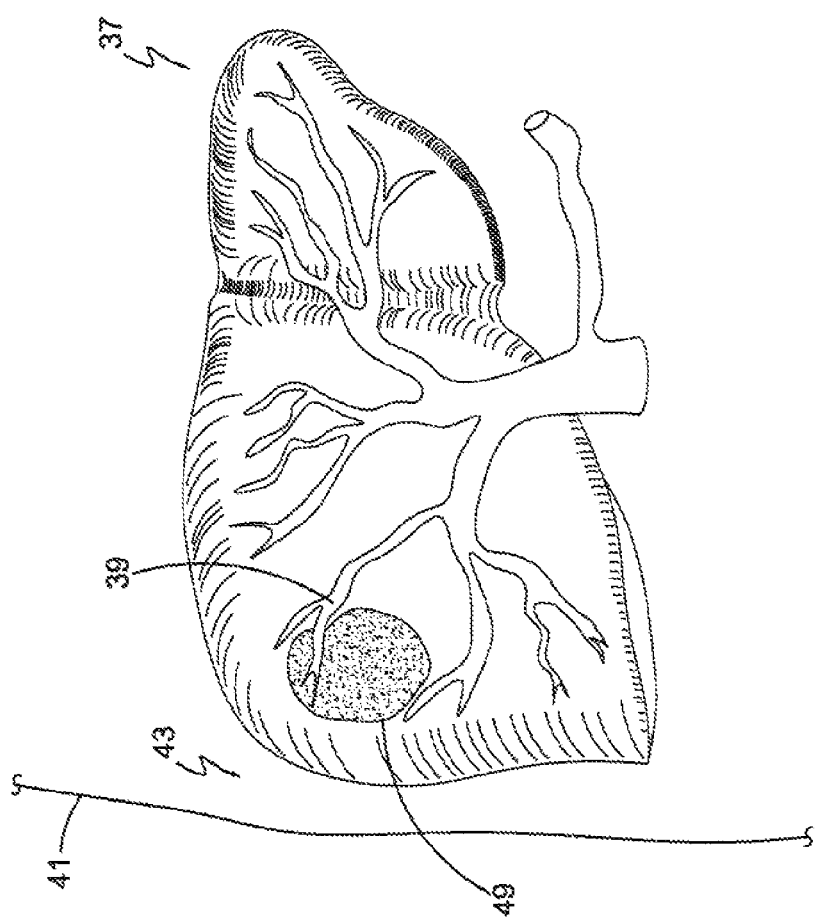
FIG. 3A is a cross-sectional view of the liver from FIG. 2B at a later time point, where the released regenerative materials have settled within the total region that was ablated with IRE energy within the liver at the start of the regenerative process.

FIG. 3A is a cross-sectional view of the liver from FIG. 2B at a later time point, where the released regenerative materials have settled within the total region that was ablated 49 with IRE energy within the liver at the start of the regenerative process. For perspective, FIG. 3A shows the liver 37 with vessels 39, the total region ablated 49, as well as interstitial space 43, and a skin surface 41 surrounding the liver.

Figure 3B:
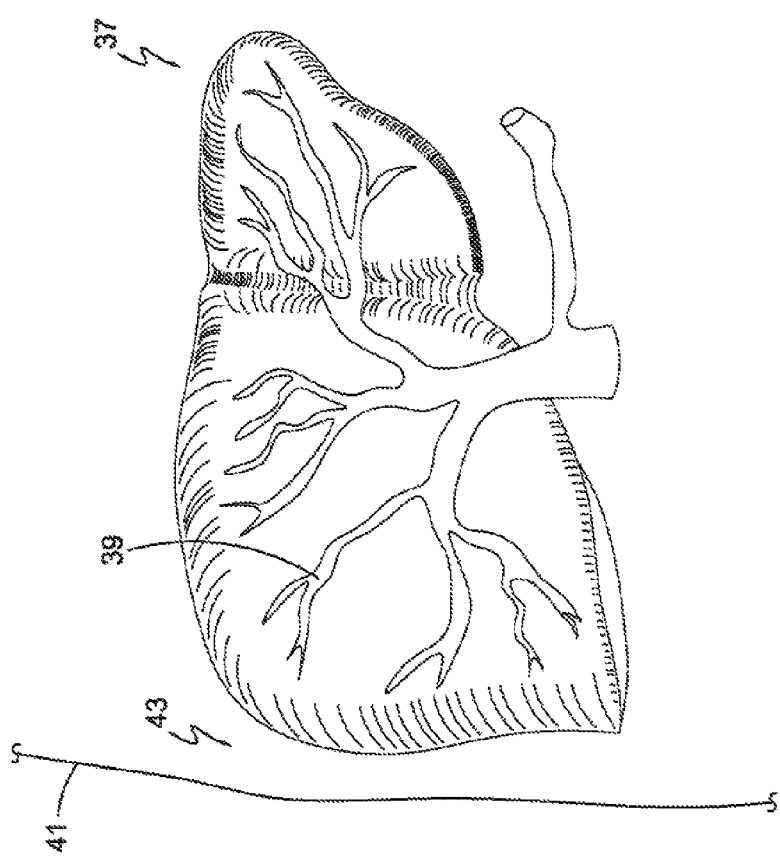
FIG. 3B is a cross-sectional view of the liver from 3A at a later time point, when the regenerative process has been completed and the liver has been restored.

FIG. 3B is a cross-sectional view of the liver from 3A at a later time point, when the regenerative process has been completed and the liver has been restored. This illustrates the liver 37, vessel 39, the interstitial space 43 outside the liver, and a skin surface 41.

Figure 4A:
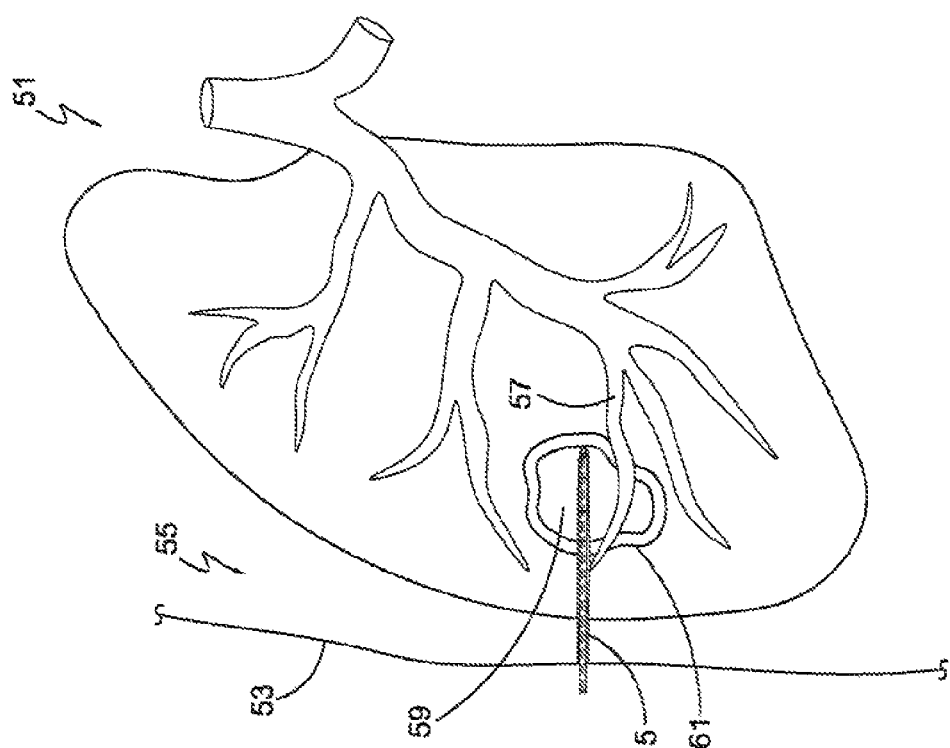
FIG. 4A depicts a cross-sectional view of a lung with a target region of tissue within the lung, where a needle of a bipolar probe coupled to an IRE power source has been inserted into the target region of tissue within the lung and where the safety zone of ablation surrounding the target region in the lung as well as interstitial space and a skin surface are shown for perspective.

Referring now to FIG. 4A, this illustrates the ablation and regeneration concerning a target region in a lung. Specifically, FIG. 4A depicts a cross-sectional view of a lung 51 with a target region 59 of tissue within the lung, where a needle 5 of a bipolar probe coupled to an IRE power source has been inserted into the target region of tissue 59 within the lung and a safety zone of ablation 61 surrounding the target region in the lung. Also shown for perspective are branches of airways 57 as well as interstitial space 55 and a skin surface 53.

Figure 4B:
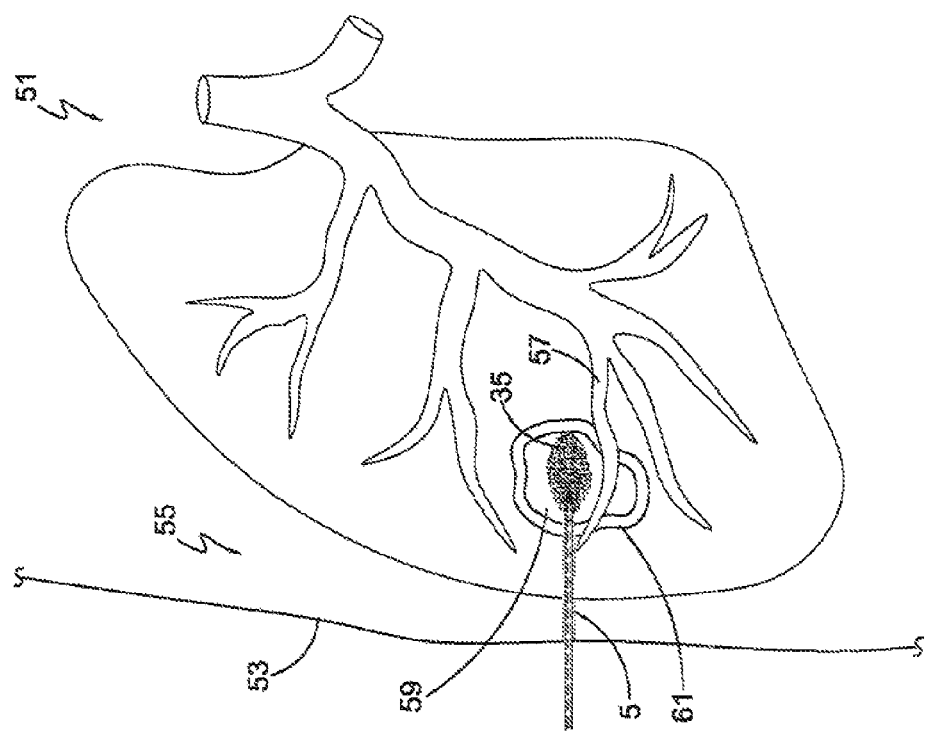
FIG. 4B is a cross-sectional view of the lung from FIG. 4A at a later time point, where IRE ablation has been performed, and regenerative materials are being released into the region that has been ablated with IRE energy within the lung through a channel in the needle of the bipolar probe.

FIG. 4B is a cross-sectional view of the lung from FIG. 4A at a later time point, where IRE ablation has been performed, and regenerative materials are being released into the region that has been ablated with IRE energy within the lung through a channel in the needle of the bipolar probe. Depicted are a lung 51 with a target region 59 of tissue within the lung, where a needle 5 of a bipolar probe coupled to an IRE power source has been inserted into the target region of tissue 59 within the lung and a safety zone of ablation 61 surrounding the target region in the lung is shown. Also shown for perspective are branches of airways 57 as well as interstitial space 55 and a skin surface 53. Also, release of the regenerative materials 35 from a channel in the needle of the bipolar probe is shown.

The use of regenerative materials released in FIG. 4B depict regeneration in relation to a lung, though this is only one example among various applications of this technology. The technology can be applied to release of regenerative materials in any of the ablation targets described in this application.

As previously indicated, in various embodiments of ablation involving the release of regenerative materials, the released materials will include stem cells. However there are various sources of stem cells that are contemplated within this technology. There are varied sources of stem cells, with a variety of methods being developed largely in response to concerns of the use of embryos by scientists in endeavors for developing stem cell lines (which in such a case would be an embryonic stem cell line). There have been significant advances recently due in part to scientists undertaking a search to establish genetically stable stem cells that are long-lived and pluripotent in nature, and that are in essence equivalent to human embryonic stem cells, but which can be established without the destruction of an embryo. The results have been an increased number of sources of stem cells and methods of producing the cells and cell lines. To this point, there are several methods and sources of stem cells.

In certain embodiments, released regenerative materials include cells of variable potencies that have been dedifferentiated. In other embodiments the cells used involve cells dedifferentiated via genetic alterations. In yet another embodiment, the cells used have been dedifferentiated through epigenetic alterations. In yet another embodiment, the cells used have been dedifferentiated through exposure to external factors, ex vivo or in situ or in vitro, or through a combination of these.

Additional embodiments of cells that may be utilized within the regenerative materials released include any or a combination of the following: stem cells derived from dead embryos in what has been termed the Landry-Zucker proposal by those in the art, stem cells derived from an embryo that lead to the destruction of the embryo, stem cells from living human embryos without harming the developmental capabilities of such embryos, and stem cells isolated or obtained through use of somatic cell nuclear transfer (SCNT). Additional embodiments include use of stem cells derived from a constructed biological artifact in a modification of SCNT method of removing an egg's nucleus and replacing it with a somatic cell nucleus in what is known as altered nuclear transfer (ANT), thereby altering the somatic cell nucleus before transfer so that the result is an artifact without essential attributes of a human embryo. Still additional embodiments involve the use of multipotent or pluripotent adult human stem cells. Additionally, variations in stem cell use may involve animal cells of various potencies for release as part of the regenerative materials. In certain embodiments, cells will be isolated from a given individual for reintroduction as part of the regenerative material into that same individual.

Additionally, in certain embodiments cells or factors to be utilized as part of or in conjunction with the release of regeneration materials include cells or factors isolated using one or more of one of magnetic beads, optical sensors, electric fields, and dielectrophoresis.

Figure 5A:
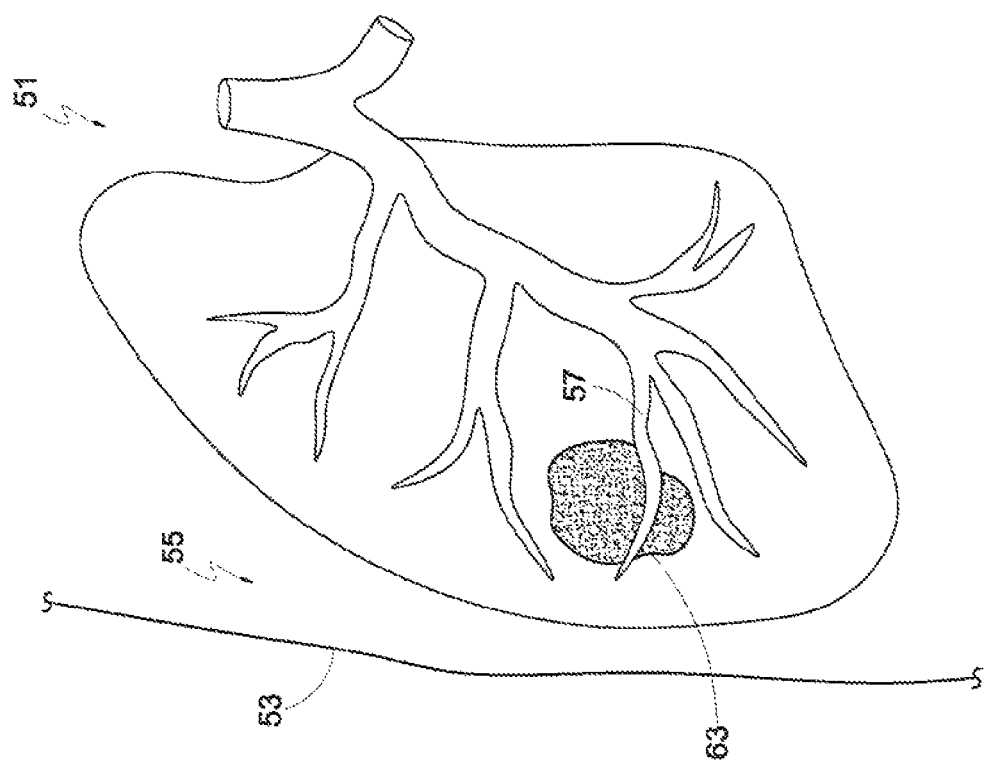
FIG. 5A is a cross-sectional view of a lung from FIG. 4B at a later time point, where the released regenerative materials have settled within the total region that was ablated with IRE energy within the lung at the start of the regenerative process.

FIG. 5A is a cross-sectional view of a lung from FIG. 4B at a later time point, where the released regenerative materials have settled within the total region that was ablated 63 with IRE energy within the lung at the start of the regenerative process. Specifically, FIG. 5A shows a lung 51 with branches of airways 57, as well as the interstitial space 55 and skin surface 53 outside the lung.

Figure 5B:
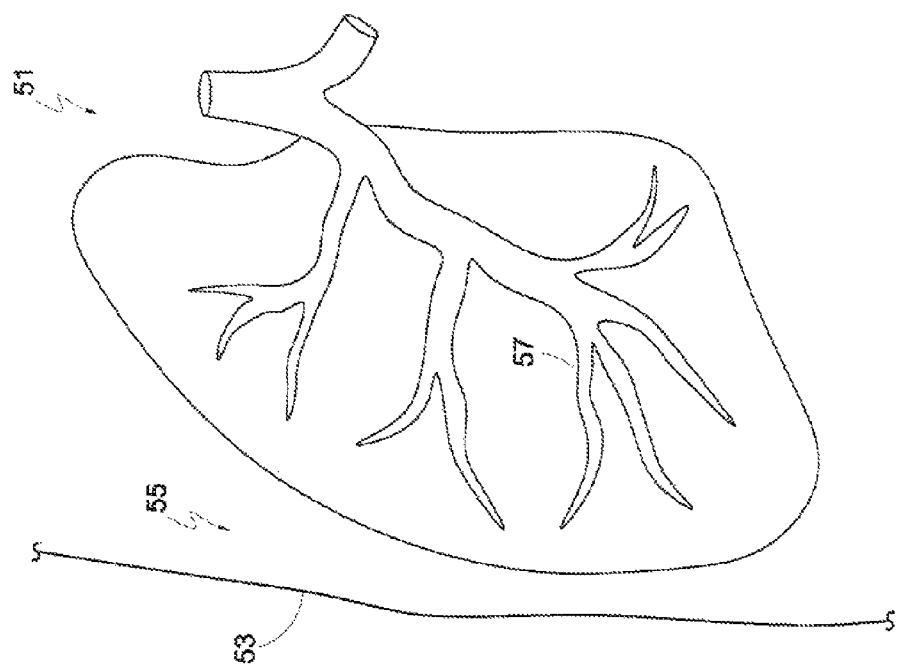
FIG. 5B is a cross-sectional view of the lung from 5A at a later time point, when the regenerative process has been completed and the lung has been restored.

FIG. 5B is a cross-sectional view of the lung from 5A at a later time point, when the regenerative process has been completed and the lung has been restored. Shown is the lung 51, the branches of airways 57, and interstitial space 55 and skin surface 53 outside the lung.

Figure 6:
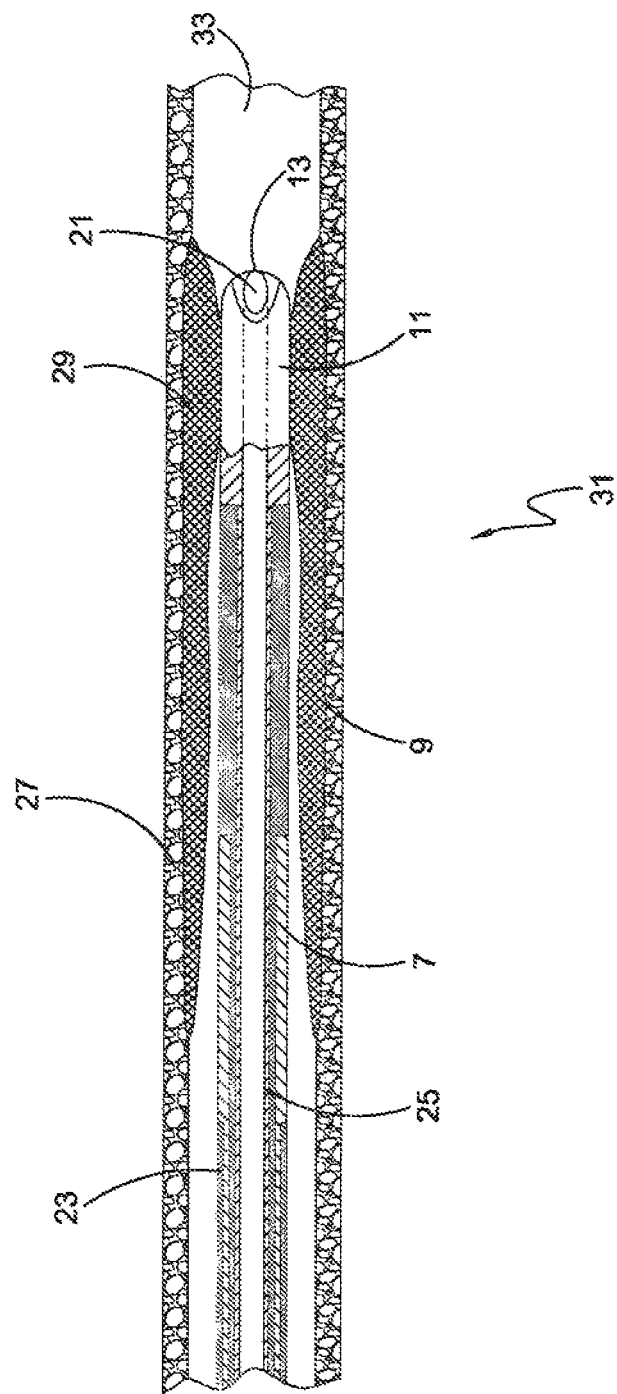
FIG. 6 depicts a cross-sectional view of a blood vessel containing a blockage and the needle of a bipolar probe within the vessel.

Referring now to FIG. 6, depicted is an enlarged cross-sectional view of a portion of the needle of the bipolar probe utilized in the current invention. Shown is a vessel 31, including an endothelial cell layer of a vessel 27, the lumen of the vessel 33, and a blockage within the vessel 29. Depicted within the vessel is the distal portion of a needle of a bipolar probe that could be utilized with IRE ablation. Indicated in the FIG. 6 are the proximal 7 and distal 11 electrodes separated by the electrode spacer 9. Also shown is the channel 21 within the probe, as well as outer insulation 23 and inner insulation 25. In this embodiment the tip 13 of the probe is shown to have a rounded or curved or dulled ending to ensure less damage to the vessel. In conceived embodiments the end could be shard or dull or rounded or curved or padded to endure proper treatment depending on the specific characteristics of the target region.

FIG. 7A illustrates a cross-sectional view of a blood vessel 31 immediately after ablation of a blockage 29 by IRE treatment using a bipolar probe shown within the vessel. FIG. 7A represents a later time point of the image shown in FIG. 6, where the blockage 29 has been ablated and the reduced material remaining will be resorbed and removed by normal physiological processes within the vessel of the patient. Also indicated are the endothelial cell layer of a vessel 27 and the lumen of the vessel 33. Depicted within the vessel is the distal portion of a needle of a bipolar probe. Indicated in the FIG. 7A are the proximal 7 and distal 11 electrodes separated by the electrode spacer 9. Also shown is the channel 21 within the probe, as well as outer insulation 23 and inner insulation 25, as well as the tip 13 of the probe.

Though a bipolar probe is shown in FIG. 7A for ablation purposes in this particular embodiment within this vessel, there are embodiments involving monopolar probes with various applications in various tissues including but not limited to applications within a vessel (including applications in any regions indicated in this application such as example embodiments including liver as well as lung, or cancerous or tumorous tissues). For example, specifically in relation to the monopolar probe configuration, one embodiment for ablation would include two monopolar probes spaced 10 mm apart, with an exposed length of up to 20 mm. Another embodiment includes a voltage of up to 2000 volts, with pulses of 100 microseconds in length being applied to a target region of tissue. An additional embodiment would involve 90 pulses provided in pulse-trains of 10, with an interval between pulses of 250 milliseconds and a time between pulse-trains of 2 seconds. The total number of pulses and pulse trains in various embodiments varies based on the effectiveness of the treatment for a given tissue. In one embodiment, the ablation zone involves two monopolar probes ablating a zone of approximately 22 mm.times.18 mm.times.12 mm, though it is understood that the ablation size and shape varies with placement of the probes and probe types, and that this is an advantage of this invention. Two single probes may also be configured so as to involve other ablation areas, including: ablation of an area of approximately 30 mm.times.25 mm.times.17 mm, including exposed electrode lengths of approximately 20 mm and a spacing of 15 mm. Such an embodiment could involve a voltage of 2500 v. It is understood that the ablation size and shape varies with placement of the probes and probe types, and that this is an advantage of this invention.

Specifically in relation to the configuration involving the bipolar probe one embodiment would include a voltage of up to 2700 v. An additional embodiment would involve 90 pulses provided in pulse-trains of 10, with an interval between pulses of 250 milliseconds and a time between pulse-trains of 2 seconds.

In one embodiment, to achieve ablation of the target region of tissue, an IRE generator is used as an IRE power source, utilizing a standard wall outlet of 110 volts (v) or 230 v with a manually adjustable power supply depending on voltage. In another embodiment the generator would have a minimum voltage of 100 v to 3000 v and be adjustable at 100 v intervals. In still another embodiment the ablation pulse applied would be between 20 and 100 microseconds in length, and be adjustable at 10 microsecond intervals. A preferred embodiment would include a generator programmable so as to operate between 2 and 50 amps, with test ranges involving even a lower maximum when appropriate. A preferable embodiment of an IRE generator would include 2 to 6 positive and negative connectors, though it is understood that this is simply a preferred embodiment and that the invention would pertain to additional embodiments understood in the art and necessary for optimal configurations for ablation.

IRE ablation can be performed with variations described in the following reference previously incorporated by reference: U.S. Patent Application Publication Number US 2007/ 0043345A1, "Tissue Ablation with Irreversible Electroporation," application Ser. No. 10/571,162. Certain embodiments involve pulses between 5 microseconds and 62,000 milliseconds, while others involve pulses of 75 microseconds to 20,000 milliseconds. In certain embodiments electrodes are spaced from 100 Volts per centimeter (V/cm) to 7,000 V/cm, while in other embodiments the spacing is 200 to 2000 V/cm as well as from 300 V/cm to 1000 V/cm. The number of pulses to be used in IRE ablation can vary. In certain embodiments the number of pulses is from 1 to 15 pulses. In other embodiments, groups of 1 to 15 pulses (here groups of pulses are also called pulse-trains) are applied in succession following a gap of time. In certain embodiments the gap of time between groups of pulses is 0.5 second to 10 seconds. Pulses can be delivered using probes, needles, and electrodes each of varying lengths suitable for use in percutaneous, laparoscopic, and open surgical procedures. Electrodes can be made a various materials known in the art and be of different sizes and shapes and be spaced at various distances from one another. Specific embodiments can be square, oval, rectangular, circular or irregular. Certain embodiments have the distance between two electrodes from 0.5 to 10 centimenters (cm), while others have from 1 to 5 cm, and yet others embodiments have from 2-3 cm. The electrode surface area can vary, and in specific embodiments the electrodes are from 0.1 to 5 square cm, and in others, from 1 to 2 square cm. The embodiments described are simply certain embodiments and are not a complete description of embodiments.

FIG. 7B is a later time point of the images seen in FIG. 7A, including a vessel 31 with a lumen 33, and inside the lumen is the distal portion of a needle of a bipolar probe. The proximal 7 and distal 11 electrodes can be seen, as well as the electrode spacer 9. In addition, FIG. 7B illustrates introduction of regenerative materials 35 into the lumen 33 of the vessel at the site of ablation.

In one embodiment the regenerative materials released into the vessel contain precursor cells capable of developing into a given cell type intended for reintroduction or regrowth or population development or redevelopment in cell number or size. Though various embodiments are described here in relation to ablation and in relation to a vessel as an example, such precursor cells could be utilized via any of the tissue types described for targeting in this writing for the same purpose, for any of various regenerative treatments.

In various embodiments the introduced regenerative materials include endothelial cell precursors or precursors from tissues such as but not limited to blood, bone, or muscle (such as satellite cells as well as mesodermal-stromal cells). There are tissue specific stem cells at various places in the body, including satellite cells in muscle (as has been described in Rando T. A. Stem Cells, Aging and the Quest for Immortality. Nature. Vol. 441(7097):1080-1086 (2006) incorporated by reference) and mesodermal stromal cells (MSCs) that are bone-marrow derived (Described in the following reference hereby incorporated by reference: Hermann A., Maisel M., Storch A., Epigenetic Conversion of Human Adult Bone Mesodermal Stromal Cells into Neuroectodermal Cell Types for Replacement Therapy of Neurodegenerative Disorders, 6(7) Expert Opinion on Biological Therapy 6(7):653 (2006))

In other embodiments the introduced regenerative material includes one or more isolated cells containing the gene for, capable of expressing, expressing, or differentially expressing singly or in combination VE Cadherin (CD144), Von-Willibrand Factor, thrombomodulin (CD141), PAL-E, PECAM-1 (CD31), CD146, VEGF Receptor-1 (FLT-1), VEGF Receptor-2, VEGF Receptor-3, TIE-1 (C-Terminus), TIE-1 (N-terminus), TIE-2, CD34, ICAM-1 (CD54), P-Selectin (CD62P), and Anti-Endoglin (CD105). Embodiments include cells with various homologues of the listed materials as well as other known RNA splice variations and isoforms.

In still additional embodiments the introduced regenerative material includes one or more of cells containing the gene for, capable of expressing, expressing, or differentially expressing singly or in combination neural cell adhesion molecule (N-CAM), fetal antigen 1 (FA1), Pax7, Asb5, IgSF4, Hoxc10, Myf5, Neuritin, Klra18, as well as MyoD target genes (such as Pw1, Dapk2, Sytl2, and NLRR1). Embodiments include cells with various homologues of the listed materials as well as other known RNA splice variations and isoforms.

In still additional embodiments the introduced regenerative material includes one or more of cells containing the gene for, capable of expressing, or expressing, or differentially expressing singly or in combination STRO-1, HOP-26 (CD63), CD49a and SB-10 (CD166), CD13, CD29, CD44, CD73, CD90, Cadherin-11, Cairetinin, CD10, CD117, Desmin, Endoglyx-1, Endosialin (TEM1, CD248), Fibroblast-Activation Protein (FAP), Laminin gamma2 chain, Neural Ganglioside GD2, Nucleostemin, Snep (stromal nidogen extracellular matrix protein), and Tenascin. Embodiments include cells with various homologues of the listed materials as well as other known RNA splice variations and isoforms.

In still additional embodiments the introduced regenerative material includes one or more of cells containing the gene for, capable of expressing, expressing, or differentially expressing singly or in combination known pluripotent stem cell markers as: Alkaline Phosphatase, Alfa-fetoprotein (AFP), Bone-Morphogenic Protein-4, Brachyury, Cluster Designation 30 (CD30), Cripto (TDGF-1), GATA-4 gene, GCTM-2, genesis, Germ Nuclear Factor, Hepatocyte Nuclear Factor-4 (HNF-4), Nestin, Neuronal Cell Adhesion Molecule (N-CAM), Oct-4, Pax-6, Stage Specific Embryonic Antigen-3 (SSEA-3), Stage Specific Embryonic Antigen-3 (SSEA-4), Stem Cell Factor (SCFor C-Kit Ligand), Telomerase, TRA-1-60, TRA-1-81, and Vimentin.

Introduced regenerative materials include in certain embodiments single or multiple infusions or injections that include sources of materials from autogeneic, isogeneic, allogeneic, and xenogeneic sources, and can include of one or more of cell types from one or more species such as mouse, rat, guinea pig, hamster, rabbit, dog, cow, as well as horse. Additional embodiments include additional mammals that are known in the art and which are routinely used for isolation of cellular tissue for the development of cell lines and for uses in research and medical procedures.

Figure 8:
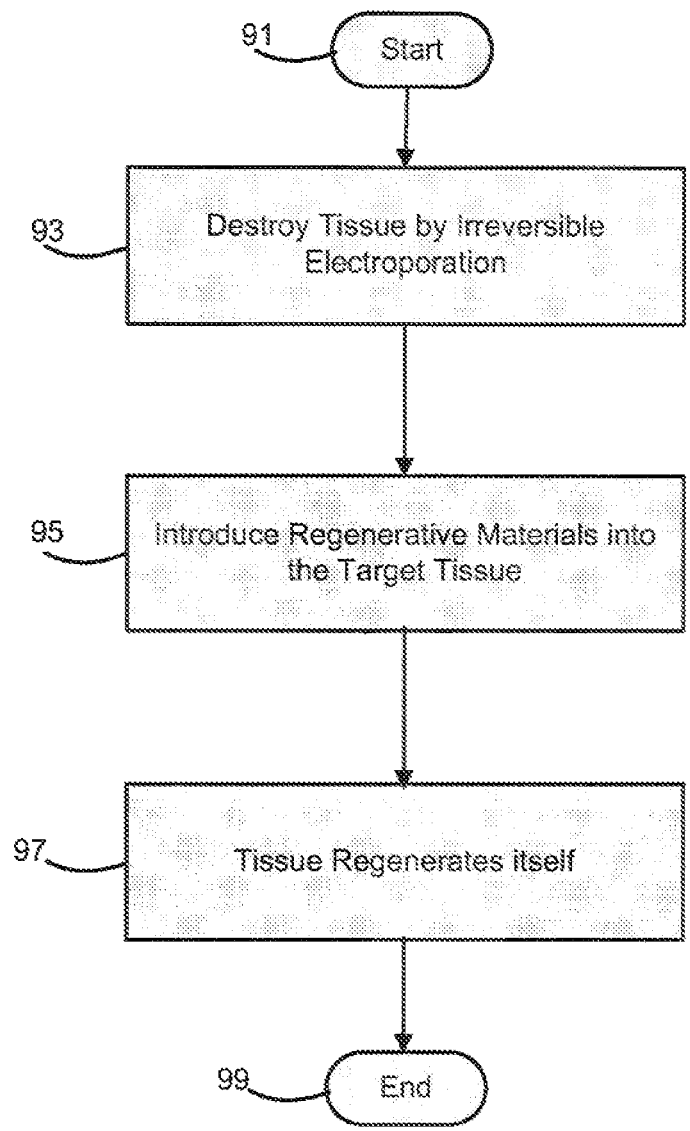
FIG. 8 depicts a flowchart showing a method of ablating a target region and inducing tissue regeneration.

FIG. 8 depicts a flowchart showing a method of ablating a target region and inducing tissue regeneration. At the start 91 of the method tissue is destroyed by irreversible electroporation 93. Regenerative materials are introduced into the area of the target tissue 95, the tissue regenerates itself 97 and the ablation and regeneration comes to an end 99.

Figure 9:
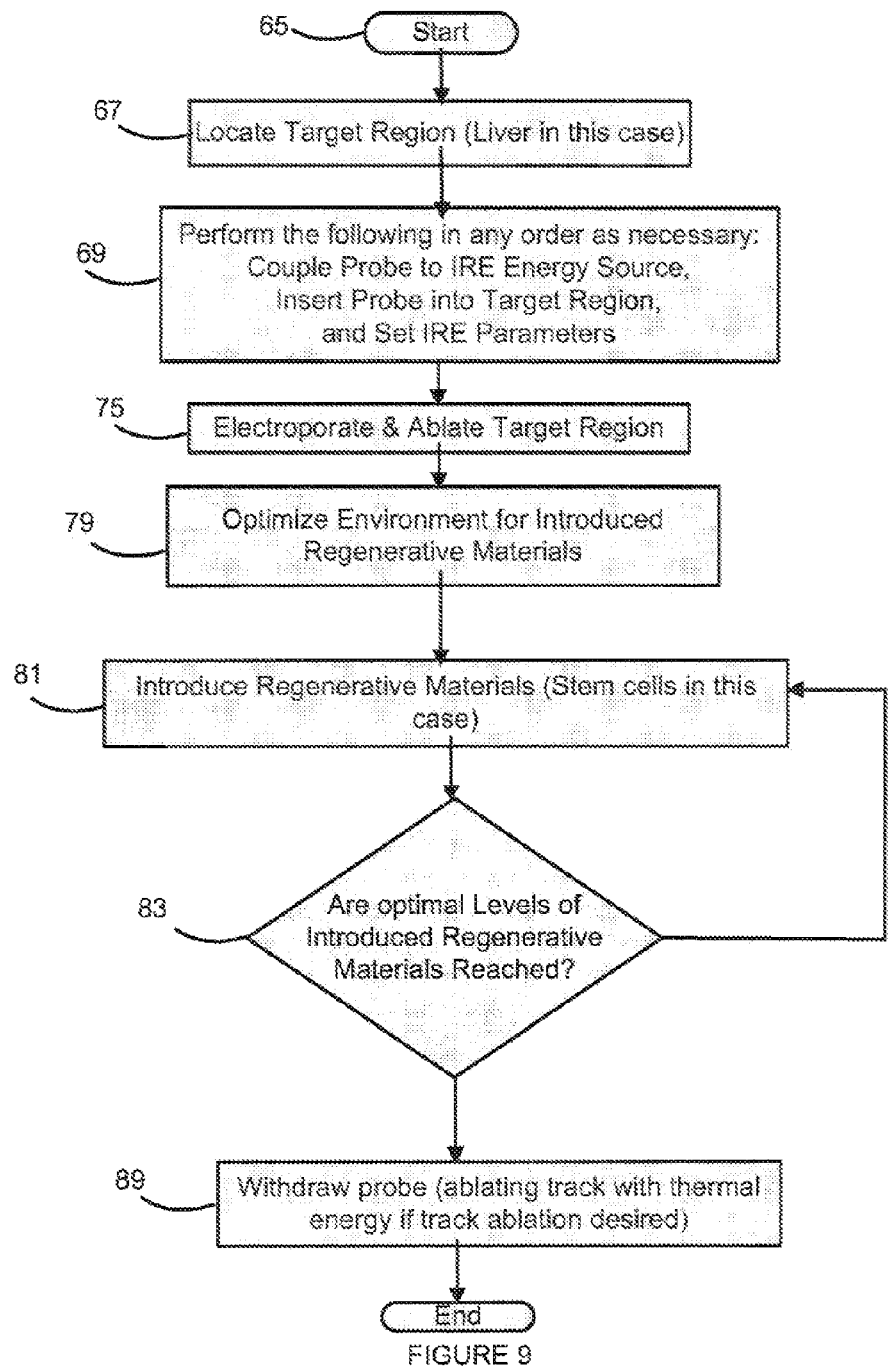
FIG. 9 depicts a flowchart showing a method of ablating a target region within a tissue such as a liver, as well as the introduction of materials capable of inducing tissue regeneration such as a regenerative solution that contained stem cells.

FIG. 9 depicts a flowchart showing a method of ablating a target region within a tissue such as a liver, as well as the introduction of materials capable of inducing tissue regeneration such as a regenerative solution that contained stem cells. At the start 65 of the method the target region is located 67. Though in this shown embodiment a tumor is indicated as the target region within a liver, this is only one example and various embodiments may include any herein described target region. In any order as necessary, the probe is coupled to the IRE power source, the probe is inserted into the target region, and IRE parameters are set 69. IRE electroporation and ablation of the target region is undertaken 75. The environment at the site of ablation is then optimized for the introduction of regenerative materials 79. In various embodiments this may involve actively or passively rebalancing tissue levels of materials by adding water, ions, or factors such as hormones, paracrine-type agents, or pharmacological mediators such as vasoreactive elements. The regenerative materials are added (in this embodiment stem cells) 81 and the question is asked as to whether optimal levels of regenerative materials have been reached 83. If the optimal level has not been reached, additional materials will be added. Once the optimal level of regenerative material has been reached the probe is withdrawn 89, using thermal energy in track ablation in an example embodiment.

In various embodiments the effect of irreversible electroporation can be brought about using a power source of Direct Current (DC). In various embodiments one or more power sources can be used so as to effect irreversible electroporation in a target region and singly or in combination also effect radiofrequency ablation, thermal electric heating, and traditional heating methods with electrodes using direct current or alternating current. These combinations of treatment can be used for additional energy output to have an effect on the target region or on a track to be ablated when the probe is withdrawn to ensure no cells are drawn from the target region towards the patient skin surface as well as allowing coagulation when desired to prevent bleeding.

There exists a need in the art for a method and apparatus that advances regeneration following tissue ablation and that can be used in a wide variety of treatments for a variety of conditions. This method and apparatus provides the significant advantages of allowing for a nonthermal, focal ablation with tissue sparing providing a foundation for which regenerative materials can be most effective. The method of utilization of nonthermal IRE ablation of target regions of tissue and the introduction of regenerative materials may be used in conjunction with additional methods and devices and for the benefit of the patient.

The invention claimed is:

1. A method of treating a target region of tissue in a living mammal by electrical ablation comprising:
   positioning in the target region a shaft comprising at least one electrode integral to the shaft, and at least one lumen adapted to receive at least one regenerative material;
   applying a plurality of electrical pulses through the electrode in an amount sufficient to induce cell death by irreversible electroporation in the target region;
   introducing through the shaft lumen the at least one regenerative material to the target region after the step of applying a plurality of electrical pulses.

2. The method of claim 1, further comprising, after the step of introducing, withdrawing the shaft while ablating tissue cells around the shaft.

3. The method of claim 2, wherein the step of withdrawing includes generating thermal energy around the shaft using radio frequency ablation.

4. The method of claim 1, wherein the step of positioning includes inserting the shaft into a tubular body part.

5. The method of claim 4, wherein the step of inserting the shaft includes inserting the shaft into a blood vessel.

6. The method of claim 1, prior to the step of introducing the at least one regenerative material, further comprising releasing at least one factor to the target region.

7. The method of claim 6, wherein the step of releasing includes releasing as a factor at least one of water, ions, hormones, paracrine agents, pharmacological mediators and vasoreactive elements.

8. The method of claim 1, wherein the step of introducing the at least one regenerative material includes using a programmable infusion pump to insert a pre-programmed amount of the regenerative material into the target region of tissue.

9. The method of claim 1, further comprising using a temperature controller to maintain the temperature of the regenerative material contained in a container at a selected temperature.

10. The method of claim 1, wherein the step of positioning includes positioning the shaft in one of digestive, skeletal, muscular, nervous, endocrine, circulatory, reproductive, integumentary, lymphatic, urinary, and soft tissue.

11. The method of claim 1, wherein the step of introducing includes introducing, as the regenerative material, at least one of totipotent, pluripotent, multipotent, and unipotent cells.

12. The method of claim 1, wherein the step of introducing includes introducing the regenerative material that is at least one of autogeneic, isogeneic, allogeneic, and xenogeneic.

13. The method of claim 1, wherein the step of introducing includes introducing, as the regenerative material, at least one of smooth muscle cells, epithelial cells, endothelial cells, adult stem cells, vascular endothelial cell precursor cells, and mesodermal stromal cells.

14. The method of claim 1, wherein the step of introducing includes introducing, as the regenerative material, cells that are the same cell type as the primary cell type of the target region.

15. The method of claim 1, wherein the step of introducing includes introducing, as the regenerative material, one of liver cells, lung cells, pancreas cells, and bone cells.

16. The method of claim 1, wherein the step of introducing includes introducing, as the regenerative material, growth factors.

17. The method of claim 1, wherein the step of introducing includes introducing, as the regenerative material, a molecule from at least one of DNA, RNA, proteins, carbohydrates, sugars, lipids, enzymes, proteases, and steroids.

18. The method of claim 1, wherein the step of introducing includes introducing, as the regenerative material, at least one of polysaccharides, proteoglycans, hyaluronic acid, collagen, fibronectin, elastin, laminin, and integrins.

19. A method of treating a target region of tissue in a living mammal by irreversible electroporation comprising:
   positioning in the target region a shaft comprising at least one electrode integral to the shaft and at least one lumen adapted to receive at least one regenerative material;
   applying a plurality of electrical pulses through the electrode in an amount sufficient to induce irreversible electroporation of tissue cells in the target region;
   introducing through the shaft lumen the at least one regenerative material to the target region after the step of applying a plurality of electrical pulses.

20. The method of claim 19, further comprising, after the step of introducing, withdrawing the shaft while ablating tissue cells around the shaft.

21. The method of claim 19, wherein the step of withdrawing includes generating thermal energy around the shaft using radio frequency ablation.

22. The method of claim 19, wherein the step of positioning includes inserting the shaft into a tubular body part.

23. The method of claim 22, wherein the step of inserting the shaft includes inserting the shaft into a blood vessel.

24. The method of claim 19, wherein the step of introducing the at least one regenerative material includes using a programmable infusion pump to insert a pre-programmed amount of the regenerative material into the target region of tissue.

25. The method of claim 19, further comprising using a temperature controller to maintain the temperature of the regenerative material contained in a container at a selected temperature.

26. The method of claim 19, wherein the step of introducing the at least one regenerative material includes introducing a molecule from at least one of DNA, RNA, proteins, carbohydrates, sugars, lipids, enzymes, proteases, and steroids.

\* \* \* \* \*